United States Patent
Attinger et al.

(10) Patent No.: US 6,527,736 B1
(45) Date of Patent: Mar. 4, 2003

(54) DEVICE FOR USE IN OPHTHALMOLOGIC PROCEDURES

(75) Inventors: Jürg Attinger, Stein am Rhein; Werner Maag, Glarus; Lorenz Egli, Neuhausen, all of (CH)

(73) Assignee: Grieshaber & Co. AG Schaffhausen, Schaffhausen (CH)

(*) Notice: Subject to any disclaimer, the term of this patent is extended or adjusted under 35 U.S.C. 154(b) by 163 days.

(21) Appl. No.: 09/694,214

(22) Filed: Oct. 23, 2000

(51) Int. Cl.$^7$ ................................................ A61M 3/00
(52) U.S. Cl. .............................. 604/43; 604/22; 604/35; 600/568; 606/171
(58) Field of Search .............................. 604/43, 35, 39, 604/22, 117, 118, 119, 164.02, 289, 290, 294, 27; 600/568; 606/170, 171

(56) References Cited

U.S. PATENT DOCUMENTS

| | | |
|---|---|---|
| 4,210,146 A | 7/1980 | Banko |
| 4,314,560 A | 2/1982 | Helfgott et al. |
| 4,589,414 A | 5/1986 | Yoshida et al. |
| 5,411,513 A | 5/1995 | Ireland et al. |
| 5,487,725 A * | 1/1996 | Peyman ........................ 604/22 |
| 5,547,473 A * | 8/1996 | Peyman ........................ 604/27 |
| 5,643,304 A * | 7/1997 | Schechter et al. .......... 606/171 |
| 5,669,876 A * | 9/1997 | Schechter et al. ............. 604/22 |
| 5,833,643 A | 11/1998 | Ross et al. |
| 5,843,111 A * | 12/1998 | Vijfvinkel .................... 606/171 |
| 6,051,011 A * | 4/2000 | Weidenbenner ............. 606/171 |
| 6,077,285 A * | 6/2000 | Boukhny ....................... 604/22 |
| 6,117,149 A * | 9/2000 | Sorensen et al. ........... 606/170 |
| 6,258,111 B1 * | 7/2001 | Ross et al. ................... 606/171 |
| 6,296,638 B1 * | 10/2001 | Davison et al. ............... 604/35 |

* cited by examiner

*Primary Examiner*—Teresa Walberg
*Assistant Examiner*—Fadi H. Dahbour
(74) *Attorney, Agent, or Firm*—Henry M. Feiereisen; Ursula B. Day

(57) ABSTRACT

A cutting device for ophthalmologic surgery in the eye of a living being specifically for suctioning, cutting and removing portions of the vitreous humor of the eye and/or tissue particles, includes a housing and a probe disposed thereon for insertion into the vitreous humor with the probe including a guide tube with a suction opening at its distal end and an inner tube co-axially inserted therein which is slideably movable in axial direction relative to the suction opening, and a control member configured to translate a rotational movement of the drive into a linear movement of the inner tube to thereby move the inner tube in the guide tube in the direction of the longitudinal axis from the resting position to the closing position and back to the resting position while preventing a linear movement of the inner tube at rotating drive when the inner tube is in the resting position.

22 Claims, 6 Drawing Sheets

DEVICE FOR USE IN OPHTHALMOLOGIC PROCEDURES

BACKGROUND OF THE INVENTION

The present invention relates, in general, to devices in ophthalmologic surgery, and more particularly to a surgical device for carrying out ophthalmologic procedures, in particular for suctioning, cutting and removing of portions of the vitreous humor and/or tissue particles of the eye of a living being.

U.S. Pat. No. 5,833,643 describes a device for use in surgical procedures which includes a housing with an electrical motor drive disposed therein and a tube disposed at the outside of the housing. An inner tube is arranged coaxially in the housing and connected to an aspiration line, and a wobble plate is operatively connected to a sliding sleeve which is attached to the shaft of the electrical motor drive and with which the inner tube is movable by an oscillation drive in an axial direction relative to the suction opening at the distal end of the outer tube.

In conventional devices or instruments, in particular those that are used for surgical removal of portions of the vitreous humor or removal of tissue particles from the vitreous humor of an eye, the oscillation drive not only generates undesirable vibration but also limits the device to grab, cut and withdraw only smaller pieces of tissue because opening and closing process with respect to the suction opening are simultaneous. Thus, when removing longer pieces of connected tissue, the procedural removal steps must be repeated two or more times.

SUMMARY OF THE INVENTION

It is thus an object of the present invention to provide an improved device for use in aspirating, cutting and removing of portions of the vitreous humor or tissue particles of the eye, which obviates the afore-stated drawbacks.

It is a further object of the invention to provide an improved device which does not produce vibrations that interfere with the surgical procedure and which allows rapid grasping and cutting of also larger pieces of connected tissue portions of the vitreous humor and immediate removing of these pieces.

These objects, and others which will become apparent hereinafter, are attained in accordance with the present invention by providing a housing, a guide tube disposed at the housing for insertion into a hollow space of the vitreous humor, with the guide tube having a distal end forming a suction opening, an inner tube received coaxially in the guide tube, a drive, and a control member operatively connected with the drive for moving the inner tube in the direction of the longitudinal axis between a resting position in which the suction opening of the guide tube is cleared to allow withdrawing the vitreous humor and/or tissue particles and a closing position in which the suction opening is sealed, said control member being configured to allow a movement of the inner tube in the guide tube in the direction of the longitudinal axis from the resting position to the closing position and back to the resting position by translating a rotational movement of the drive into a linear movement of the inner tube, and to refrain from acting on the inner tube at rotational movement of the drive when the inner tube is in the resting position.

In accordance with the invention, the device (high-speed cutter) does not produce vibrations that interfere with the surgical procedure and is able to reliably and quickly grab also larger pieces of connected tissue of the vitreous humor for subsequent removal. In operation, independently of the cutting frequency, the suction opening of the device according to the invention can be held in open position for a relatively long period to enable optimal aspiration, whereas closing and cutting of the differently shaped and dimensioned portions of the vitreous humor and the tissue particles can be carried out rapidly even when a great amount of material is being cut and removed.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
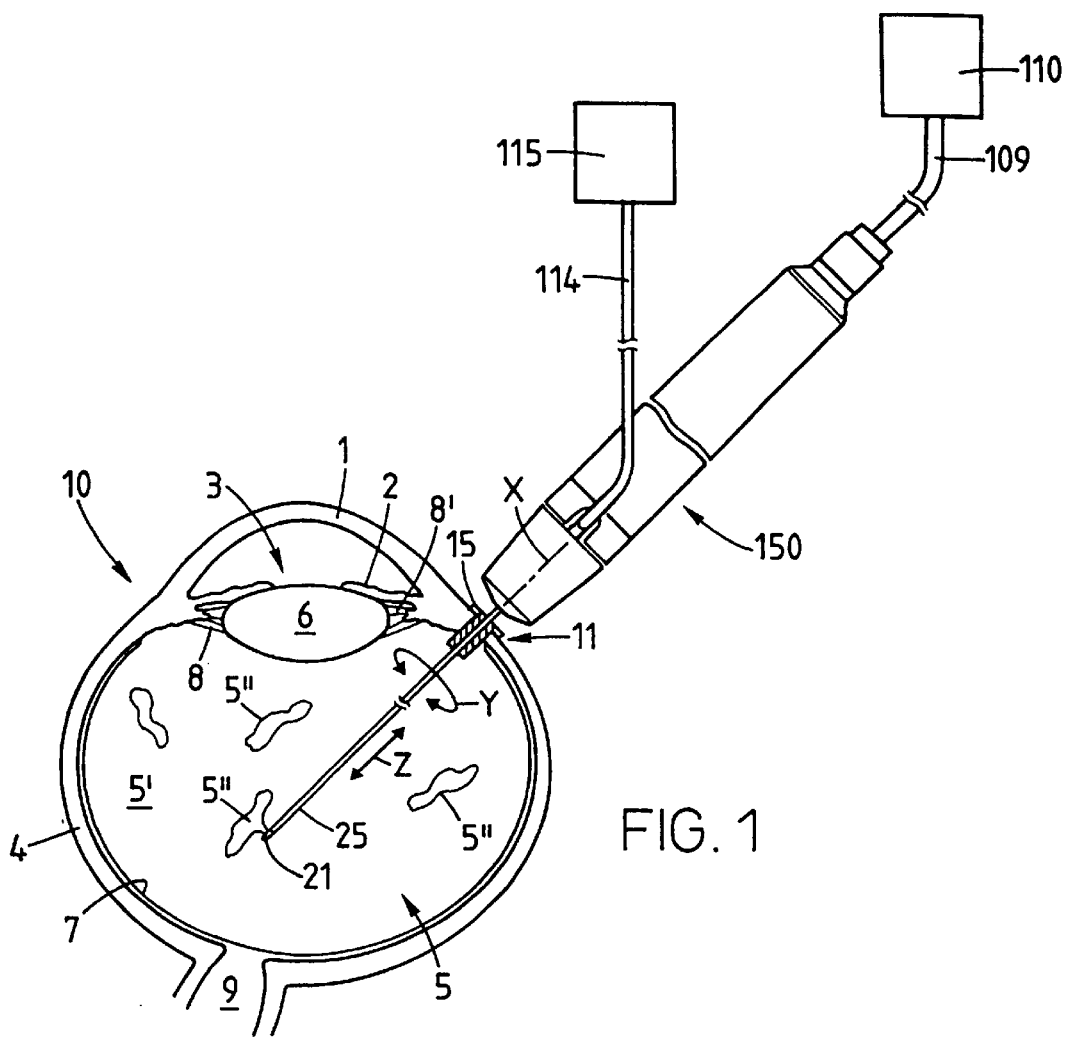
FIG. 1 is a horizontal sectional view of an eye and a schematic illustration of a device according to the present invention, showing a probe for aspirating, cutting and removing portions of the vitreous humor and/or tissue particles from the cavity of the vitreous humor.

Throughout all the Figures, same or corresponding elements are generally indicated by same reference numerals.

Turning now to the drawing, and in particular to FIG. 1, there is shown an enlarged schematic illustration of a horizontal sectional view of an eye 10 showing the cornea 1, the iris 2, the pupil 3, the sclera 4 and the vitreous humor 5 and the vitreous humor space 5', the lens 6, the retina 7, the ciliary body 8 with the zonula fibers 8' and the optical nerve bundle 9. Further shown in FIG. 1 is a schematic device 150 which has a probe 25 for insertion into the vitreous humor space 5'. At the front end, the elongated tubular probe 25 has a recess 21 shown schematically and configured for grasping and cutting portions 5" of the vitreous humor and/or tissue particles as well as subsequent removal from the vitreous humor space 5'. The device 150 and the probe 25 can be turned manually about a longitudinal axis X in the direction of Y and moved in the direction of double arrow Z in axial direction. To prevent injury, the device 150 with the probe 25 can be inserted into a sleeve 15 inserted or disposed in the sclera 4 in the area of the pars plana 11.

The device 150 is operatively connected to a drive unit 110 (shown schematically only) via an electric line 109 and to an aspiration unit 115 via an aspiration line 114 (shown schematically only). Operation and control of drive unit 110 and the aspiration unit 115 is effected, for example, by means of a pedal switch or a similar switch (not shown).

Figure 2:
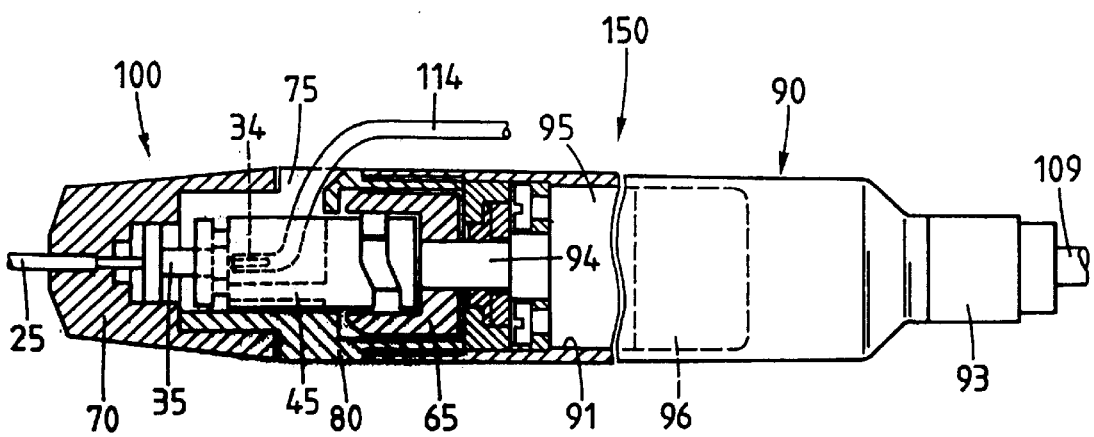
FIG. 2 is an enlarged partial sectional view of the device of FIG. 1, with the housing configured as a handle and integrated drive system.

As shown in FIG. 2, the device 150 includes a hollow cylindrical housing 90, which is configured as a handle, and a drive system, generally designated by reference numeral 100 and fitted in the housing 90. At its rearward end, the housing 90 has a cap 93 for attachment of the electric line 109. The cap 93 may be secured to the housing, for example, by a screwed connection (not shown). The housing 90 has an interior space 91 for accommodating a drive 95, for example, an electric motor, and a rotation sensor 96 mounted to one end of the drive 95. At its other end, the drive 95 has a shaft 94 which rotates about the longitudinal axis X (FIG. 3), with a fork-shaped rotation body 65 being mounted on the shaft 94.

The drive system 100 as shown in FIG. 2, includes essentially the rotation sensor 96 disposed in the housing 90 and the electric motor drive 95 with the shaft 94, the rotation body 65 connected to the shaft 94, and a control member 45 which is in operative engagement with the rotation body 65 and a coupling member 35 which is operatively connected to the probe 25. The rotation body 65 and the control member 45 as well as the coupling member 35 are disposed in coaxial relation in an intermediary piece 80 which is attached to the housing 90 by a screw connection. Mounted to the front end of the intermediary piece 80 is a headpiece 70 which carries the probe 25, for example, via quick-release lock. The coupling member 35 has a connection piece 34 at one end for attachment of the aspiration line 114 in any suitable manner. The aspiration line 114 is guided through a recess 75 in the intermediary piece 80 outwardly for connection to the aspiration unit 115 (FIG.1).

In accordance with FIG. 2, the headpiece 70 is pushed in axial direction over the intermediary piece 80 and turned by 90° relative to the intermediary piece 80 for realizing a secure connection via the quick-release lock.

Figure 3:
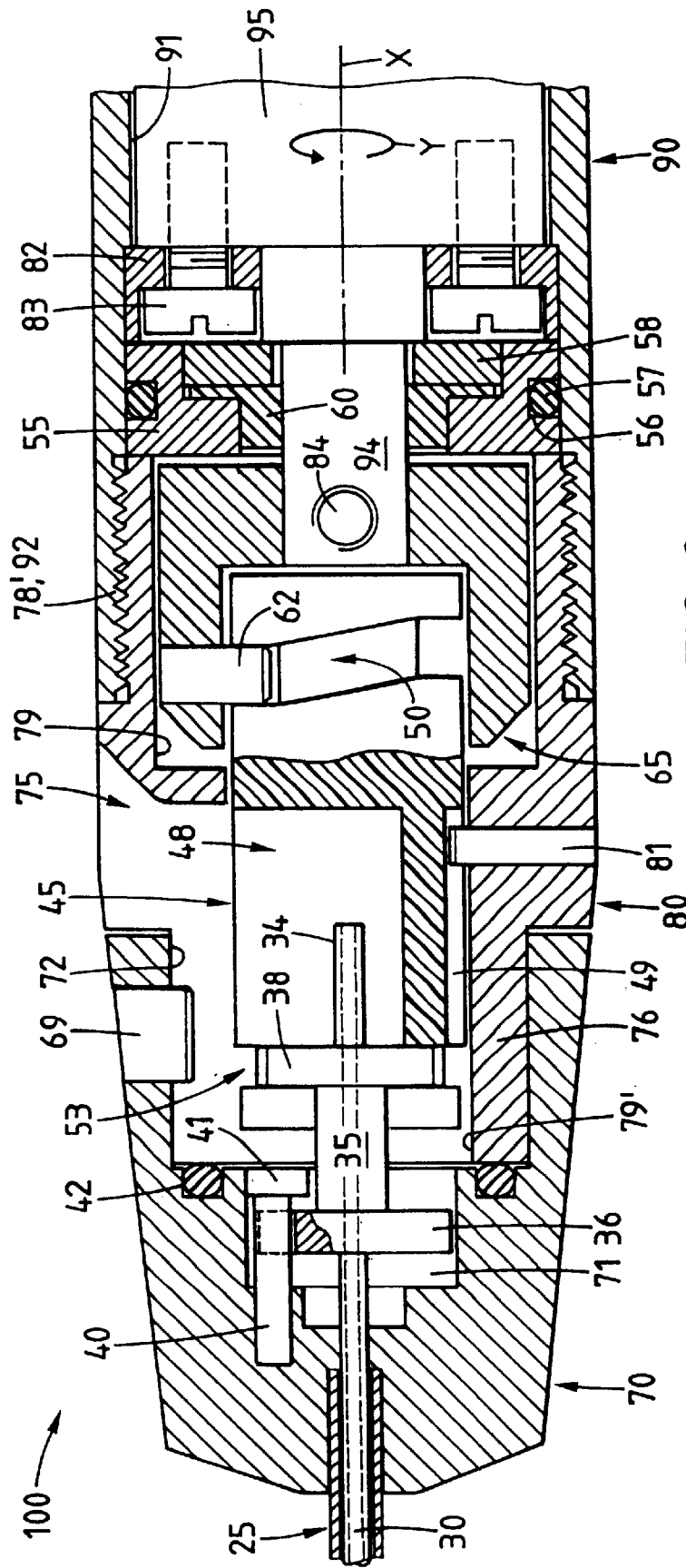
FIG. 3 is an enlarged sectional view of the housing with integrated drive system for interaction with the probe.

Turning now to FIG. 3, there is shown a sectional view, on an enlarged scale, of the drive system 100 disposed in the housing 90. The electric motor drive 95 is, for example, held in the interior of the housing 90 by a retainer ring 82 and screw fasteners 83. The rotation body 65 which is operatively connected to the front end of the shaft 94 by a threaded pin 84 or similar fastener, rotates about the longitudinal axis X in the direction of arrow Y when activating the drive 95. A seal 60 is mounted on the shaft 94 between the retainer ring 82 and the rotation body 65, disposed in a first recess 79 of the intermediary piece 80, and is secured against axial displacement by a disk 58 and a spacer ring 55. The spacer ring 55 has an outer annular groove 56 for receiving a seal 57, such as an O-ring, and is secured against axial displacement by the intermediary piece 80 which is threadably engaged in the housing 90.

FIG. 3 further shows the cylindrical control member 45 which is formed on one end with the curved track 50 and disposed in a second recess 79' of intermediary piece 80. A pin 62 projects inwardly from the fork-shaped rotation body 65 into the curved track 50, so that a rotation of the shaft 94 about the longitudinal axis X in the direction of Y results in movement of the pin 62 in the curved track 50 of the control member 45. The control member 45 has a recess 48 in the shape of a groove or slot, and an axial groove 49 for engagement of a pin 81 to thereby secure the control member 45 against rotation when the control member 45 moves in axial direction.

The coupling member 35 is mounted to the other end of the control member 45 and includes a plate 38 for positive engagement in a slot-shaped groove 53 of the control member 45. The coupling element 35 is further formed with a flange 36 in spaced-apart relation to the plate 38 for engagement in a first recess 71 of headpiece 70. A pin 40 with a stop member 41 is mounted to the headpiece 70 for so engaging a recess (36') in the outer circumference of the flange 36 that the coupling member 35, which conjointly moves in axial direction with the control member 45, is secured against rotation. The coupling member 35 thus is connected to the aspiration line 114 at one end via the connection piece 34, and at its other end in operative connection (not shown) with inner tube 30 of the probe 25.

Figure 7:
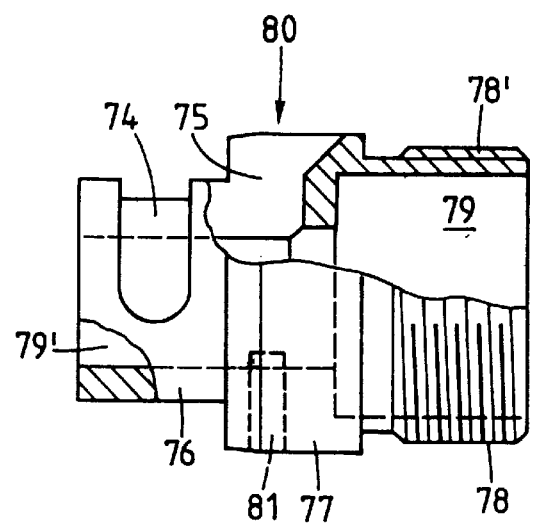
FIG. 7 is a sectional view, partially broken away, of an intermediary piece of the housing according to FIG. 3.

As shown in FIG. 3, the intermediary piece 80 has an outer thread 78' which is in mesh with the inner thread 92 of the housing 90. In assembled state, the headpiece 70 may be sealed against the intermediary piece 80, for example, by an O-ring 42 bearing upon an end face of the cylindrical segment 76 which is inserted into a recess 72 of the headpiece 70. The headpiece 70 with the elongated tubular probe 25 is detachably secured to the intermediary piece 80 by a pin-shaped locking cam 69 in the form of a bayonet-type locking mechanism. In FIG. 3, the headpiece 70 is coupled to the intermediary piece 80 and a rotation of the headpiece 70 about an angle of 90° about the longitudinal axis X results in a locked engagement of the locking cam 69 in a bore 74 of the intermediary piece 80. (FIG. 7).

Figure 4:
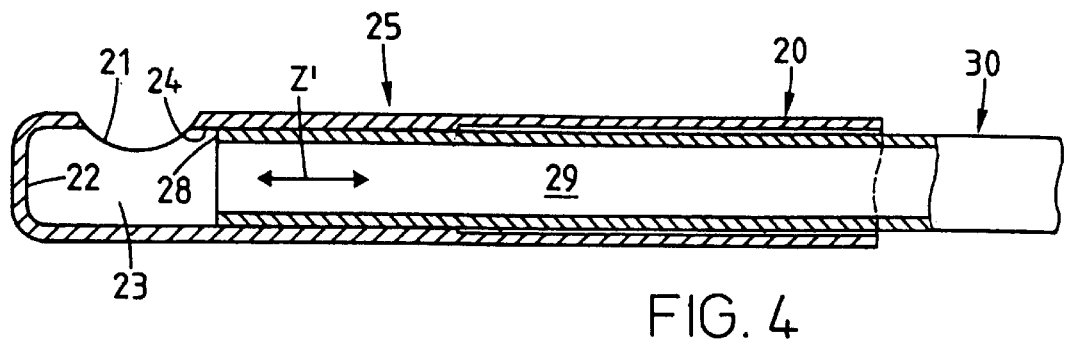
FIG. 4 is an enlarged partial sectional view of the probe of the device as shown in FIG. 1, with an inner tube arranged coaxially in a guide tube and occupying a resting position.

Referring now to FIG. 4, there is show an enlarged sectional view of the front end of the probe 25 which includes an outer guide tube 20 and an inner tube 30 which is received coaxially in the guide tube 20 and can move in a direction of double arrow Z'. The outer guide tube 20 is closed at its forward end by an end wall 22. At a distance to the end wall 22, the guide tube 20 has a recess 21 which is referred to in the following description as suction opening 21. To improve guidance and coaxial centering of the inner tube 30, the guide tube 20 is formed in the area of the recess 21 with axial segments 24, 24' which are provided in offset relation. FIG. 4 shows a resting position in which the inner tube 30 is retracted relative to the end wall 22 of the guide tube 20, so that the recess 21 is open to allow aspiration of tissue particles 5" (FIG. 1).

Persons skilled in the art will understand that the probe 25 is shown here in exaggerated illustration for ease of understanding. In reality, the dimensions of the probe 25 for insertion into the cavity 5' of the vitreous humor 5, are in accordance with a preferred non-limiting embodiment such that the guide tube 20 has an outer diameter of approximately 0.91 mm and the coaxial inner tube 30 has an outer diameter of approximately 0.63 mm. The suction opening 21 at the distal end of the guide tube 20 has an axial length of approximately 0.7 mm.

Figure 5:
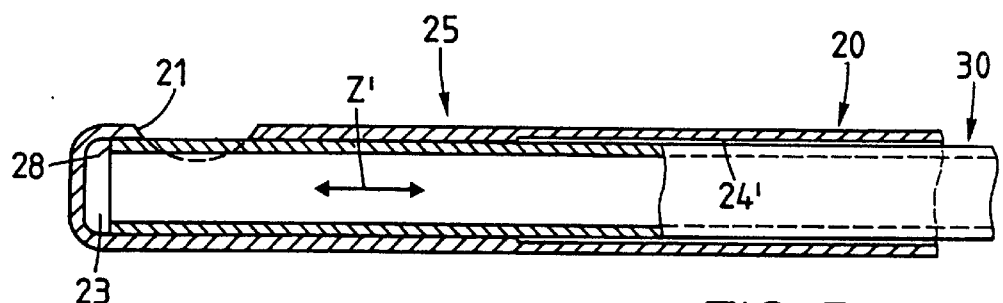
FIG. 5 is a partial view of the probe of FIG. 4, with the inner tube shifted to a closing position with respect to the suction opening.

FIG. 5 shows a closing position in which the inner tube 30 is shifted toward the end wall 22, thereby sealing the suction opening 21. The end face 28 of the inner tube 30, confronting the end wall 22 of the guide tube 20, is configured as a cutting edge (not shown here in detail) and severs tissue particles 5" (FIG. 1), drawn through aspiration via the suction opening 21 into the inner space 23 of the guide tube 20, as the inner tube 30 moves toward the end wall 22. Subsequently, the severed tissue particles 5" are forced through axial channel 29 of the inner tube 30 and removed via the aspiration line 114.

Figure 6:
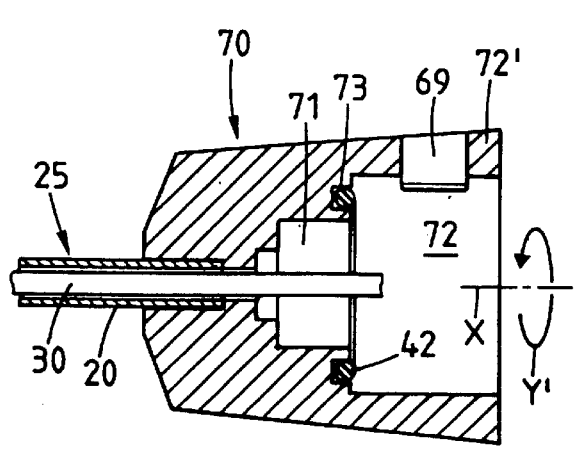
FIG. 6 is a sectional view of a headpiece for attachment to the housing according to FIG. 3.

FIG. 6 shows a sectional view of the headpiece 70 and the probe 25 attached thereto. The guide tube 20 may be secured to the headpiece 70 by gluing or any other suitable manner. The headpiece 70 has a forward cylindrical recess 71 and a rearward cylindrical recess 72 of greater diameter than the recess 71, thereby defining a shoulder formed with a ring groove 73 for receiving the seal 42 (FIG. 3). A locking pin 69 is suitable secured in a circular wall section 72' of the headpiece 70 and projects inwardly from the circular wall 72' into the recess 72.

Turning now to FIG. 7, there is shown a partially broken away view of the intermediary piece 80 which includes a first cylindrical segment 76, a second cylindrical segment 77 and a third segment 78 integrally formed with the segment 77 and provided with an outer thread 78'. The intermediary piece 80 has a first cylindrical axial recess 79 of relatively greater diameter and a second cylindrical recess 79' of relatively smaller diameter. Further shown in FIG. 7 is the approximately slot-shaped axial recess 75 for receiving the aspiration line 114. (FIG. 2). A pin 81 is suitably secured to the segment 77 and projects inwardly from the segment 77 into the recess 79', for securing the control member 45 (FIG. 3) against rotation when the pin 81 projects into the recess 79' of the intermediary piece 80.

The first cylindrical segment 76 of the intermediary piece 80 is provided with a bore 74 which extends partially in circumferential direction. The bore 74 is configured so that the headpiece 70, which can be pushed over the first cylindrical segment 76, engages with the locking cam 69 in bore 74 so that a turning of the headpiece 70 about the longitudinal axis X at an angle of about 90° in the direction of arrow Y' results in a secure attachment the intermediary piece 80 as a result of the afore-mentioned bayonet-type locking mechanism which permits a rapid release of the headpiece 70 from the intermediate piece 80, and the housing 90, when cleaning and/or disinfecting of the probe 25 and/or a replacement of the entire headpiece 70 is desired.

Figure 8:
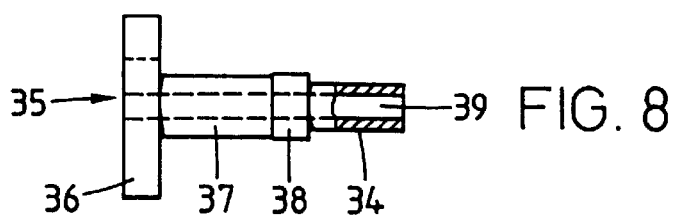
FIG. 8 is a partial sectional view of a coupling member for connection to the drive system according to FIG. 3.

FIG. 8 is a detailed view of the coupling member 35 which includes a cylindrical core 37 having formed therein a throughbore 39 and carrying in spaced-apart relationship the front flange 36 and the plate 38. The rearward end of the cylindrical core 37 is configured as a cylindrical connecting piece 34 which is offset for attachment of the aspiration line 114 (FIG. 2).

Figure 8A:
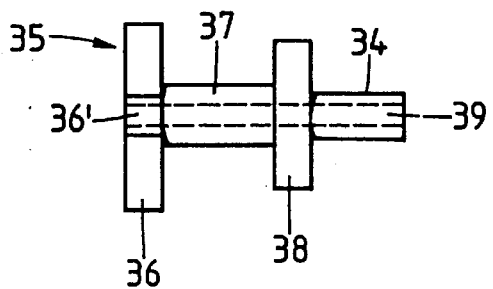
FIG. 8A is a plan view of the coupling member as shown in FIG. 8.
Figure 8B:
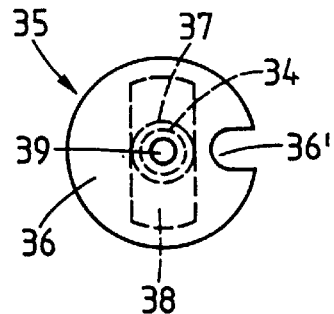
FIG. 8B is a side view of the coupling member of FIG. 8A.

The coupling piece 35 is shown in FIG. 8A in plan view and in FIG. 8B in side view, showing the flange 36 which is configured as a circular disk with the recess 36' at its outer circumference, the cylinder core 37 with the throughbore 39 and the connecting piece 34, and the plate 38 which extends vertically and transverse to the longitudinal direction of cylinder core 37 (FIG. 8B).

Figure 9:
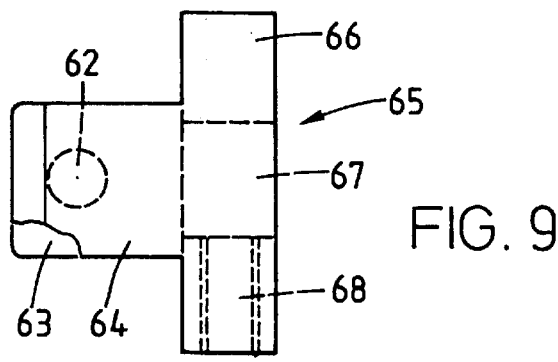
FIG. 9 is a representation of a rotation body for connection to the drive system according to FIG. 3.

FIG. 9 shows the fork-shaped rotation body 65 which includes a disk-shaped side portion 66, and two fork arms 63 and 64 formed on the side portion 66 in spaced-apart relation. The pin 62 is attached to the fork arm 63 in a suitable manner. The side portion 66 has a throughbore 67 and a threaded bore 68 extending transversely to the throughbore 67. In the assembled state, as shown in FIG. 3, the shaft 94 of the electric motor drive 95 is received in the throughbore 67 and secured by the threaded pin 84.

Figure 9A:
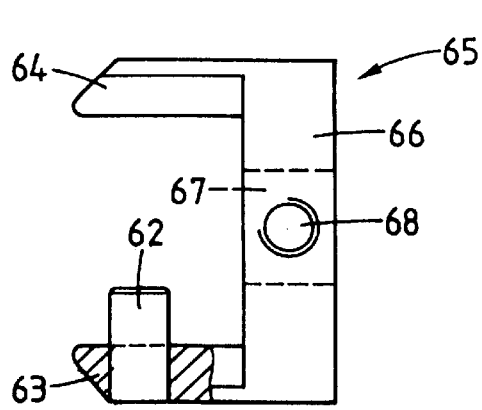
FIG. 9A is a plan view of the rotation body of FIG. 9.
Figure 9B:
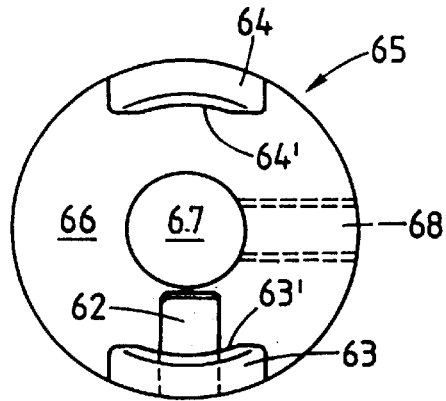
FIG. 9B is a side view of the rotation body of FIG. 9A.

FIGS. 9A, 9B show a plan view and a side view, respectively, of the rotation body 65 to illustrate again the side portion 66 with throughbore 67 and threaded bore 68. Mounted to the side portion 66 are the parallel fork arms 63 and 64, with the fork arm carrying the pin 62. The fork arms 63, 64 oppose one another on the side portion 66 to define confronting inner sides 63' and 64' which are configured of substantially circular arc shape to complement the cylindrical control member 45.

Figure 10:
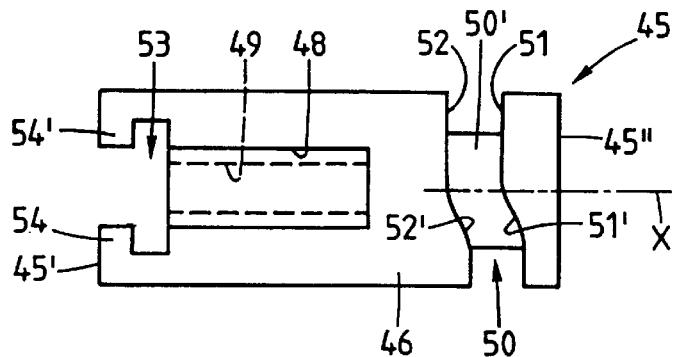
FIG. 10 is a plan view of a cylindrical control member formed with a curved track.

FIG. 10 shows a plan view of the cylindrical control member 45 which has one end formed with the groove 53 located at a distance to the end wall 45' and extending transversely to the longitudinal axis X. At its other end, the control member 45 is provided with the curved track 50 at a distance to the rear wall 45". Starting from the end wall 45', the control member 45 is further provided with an elongate axial recess and a corresponding longitude groove 49 at the outer circumference. The curved track 50 in the control member 45 is bounded by a cylindrical core 50' has an approximately groove-shaped or a slot-shaped configuration. The curved track 50 is composed in circumferential direction essentially of two circular shaped interconnected segments, with one segment having side walls 51 and 52 which are oriented orthogonal relative to the longitudinal axis X, and with the other segment having side walls 51' and 52' which are curved at an inclination in the direction of the rear wall 45" of the control member 45. The side walls 51, 52 and 51', 52' of the curved track 50 disposed circumferentially on the control member 45 are arranged in spaced apart parallel relation. The distance between the spaced-apart side walls 51, 52 and 51', 52' of the curved track 50 is so selected that the pin 62 of the rotation body 65 rotating about the longitudinal axis X is guided precisely in the track 50, thereby effecting the axial movement of the control member 45 together with the coupling member 35 and the inner tube 30.

Figure 10A:
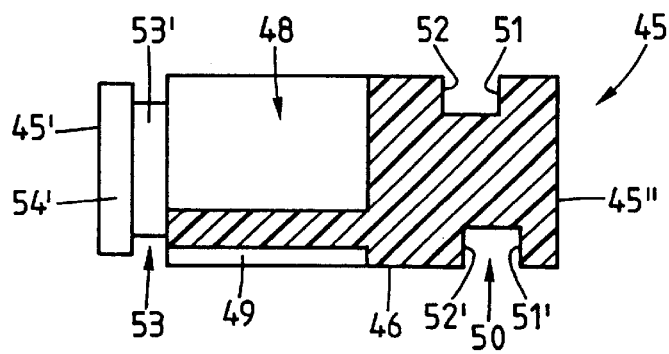
FIG. 10A is a sectional view of the control member according to FIG. 10.
Figure 10B:
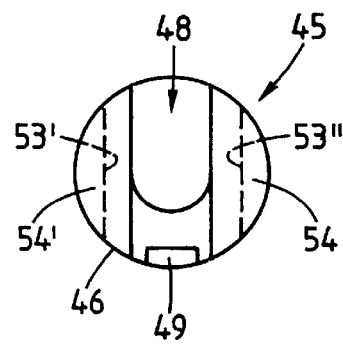
FIG. 10B is a side view of the control member of FIG. 10A.

FIGS. 10A and 10B show a longitudinal section and a side view of the control member 45, illustrating in detail the cylindrical segment 46 bounded at one end by the end wall 45' and at the other end by the rear wall 45". Spaced from the rear wall 45" is the circular curved track 50 with side walls 51, 51' and 52, 52'. The axial recess 48 is disposed in the cylindrical segment 46 and extends to the front wall 45'. As a consequence of the axial recess 48, the end wall 45' is subdivided in two wall segments 54 and 54'. At its outer circumference, the cylindrical segment 46 is further provided in axial direction with the longitudinal groove. Formed at a distance to the end wall 45' is the groove 53 which extends transversely to the longitudinal direction and is bounded by the two inner walls 53' and 53" (FIG. 10B). FIG. 10B further shows the recess 48 and the two segment-shaped wall portions 54 and 54'.

After having described the components of the device 150, its mode of operation will now be described in more detail. A reliable aspiration and cutting function requires an exact calibration and fixation of the axially movable inner tube 30 with respect to the suction opening 21. In order to attain this precondition, the rotation sensor 96 generates two phase-shifted electrical signals in dependence to the rotational movement. These signals are used, on the one hand, to detect and determine the current rotational direction of the drive 95 and, on the one hand, to detect and determine the current position (first reference point) of the inner tube 30 relative to the suction opening 21 at the distal end of the guide tube 20.

The first reference point (FIG. 4) is determined by rotating the electric motor drive 95 and thereby shifting the inner tube 30 in axial direction toward the suction opening 21 while the aspiration unit 115 is switched on, until the vacuum rises and upon reaching a second reference point (FIG. 5) and complete sealing of the suction opening 21 (FIG. 5), the absolute value of the vacuum has been reached. The axially spaced two reference points are arranged at a distance relative to each other as a result of the interaction between the shaft 94, the rotation body 65 and the control member 45 at an angle of rotation of 180° in axial direction. The first reference point establishes the resting position in which the suction opening 21 is completely open (FIG. 4), and the second reference point establishes the closing position in which the suction opening 21 is sealed.

Figure 11:
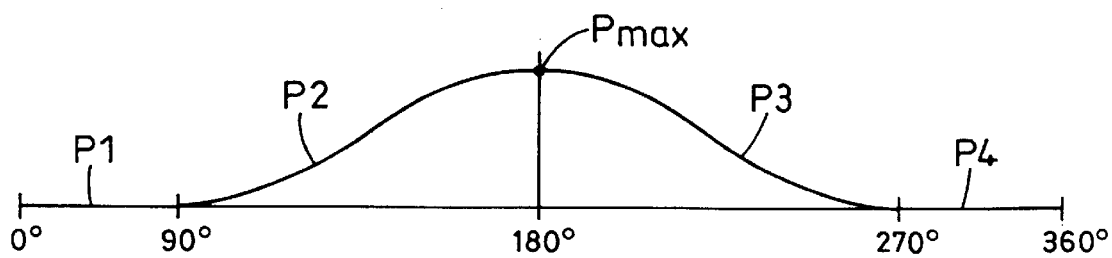
FIG. 11 is a graphic representation of the curved track of the control member of FIG. 10.

FIG. 11 is a graphical illustration of the movement pattern of the control member 45 as result of the interaction between the curved track 50 and the pin 62, as plotted in degrees of rotation. The curved track 50 is suitably configured such that when the shaft 94 together with the rotation body 65 move about longitudinal axis X in a rotation movement at an angle from 0° to 360°, the following rotation phases P1 through P 4 are realized to implement the movement pattern in axial direction of the control member 45 through interaction with the rotation body 65:

a) in the first rotation phase P1 about rotation angle from 0° to 90°, the pin 62 of the fork-shaped rotation body 65 runs idle in the curved track 50 so that no axial displacement of the control member 45 is effected, and the inner tube 30 remains stationary at a distance to the suction opening 21 (resting position);

b) in the second phase P2 about rotation angle from 90° to 180°, the control member 45 is moved by the pin 62, resulting in an axial displacement of the control member 45 and thus in a axial movement of the inner tube 30 into the closing position, designated $P_{max}$ in FIG. 11, in which the suction opening 21 is sealed;

c) in the third rotation phase P3 about rotation angle from 180° to 270°, the control member 45 with the inner tube 30 are returned in axial direction to the starting (resting) position in which the suction opening 21 is cleared again; and d) in the fourth rotation phase P4 about rotation angle from 270° to 360°, the pin 62 runs idle again so that the control member 45 is not activated and the inner tube 30 remains stationary at a distance to the suction opening 21.

During the afore-described rotation phases P1 to P4, the rotational movement of the shaft 94 is translated from the pin 62 of the rotation body 65 to the control member 45 and the inner tube 30 in such a way that during the rotation phase P1 at the rotation angle of 0° to 900°, the inner tube 30 remains in the resting position with open suction opening 21 open. In the following rotation phase P2 of rotation body 65 at rotation angle of 90° to 180°, the control member 45 with inner tube 30 is moved in axial direction for sealing the suction opening 21, and in the rotation phase P3 about rotation angle from 180° to 270°. the suction opening 21 is cleared again. The following rotation phase P4 about rotation angle from 270° to 360° is analog to rotation phase P1, so that the control member 45 with the inner tube 30 remains in the resting position with open suction opening 21. The time period of the rotational phases P1 and P4 for aspirating tissue particles is at least as long as the combined time period of rotation phases P2 and P3 for closing and subsequent reopening of the suction opening 21 in the outer guide tube 20.

It should be noted, when switching off the device 150 (FIG. 2), the electric motor drive 95 is always stopped by the rotation sensor 96 at the moment when the suction opening 21 is cleared by the inner tube 30 and thus open (FIG. 4). This ensures, that whenever the device 150 is started, tissue particles 5" can be drawn through the suction opening 21 and subsequently severed as the inner tube 30 moves axially relative to the suction opening 21 of the outer guide tube 20.

Figure 12:
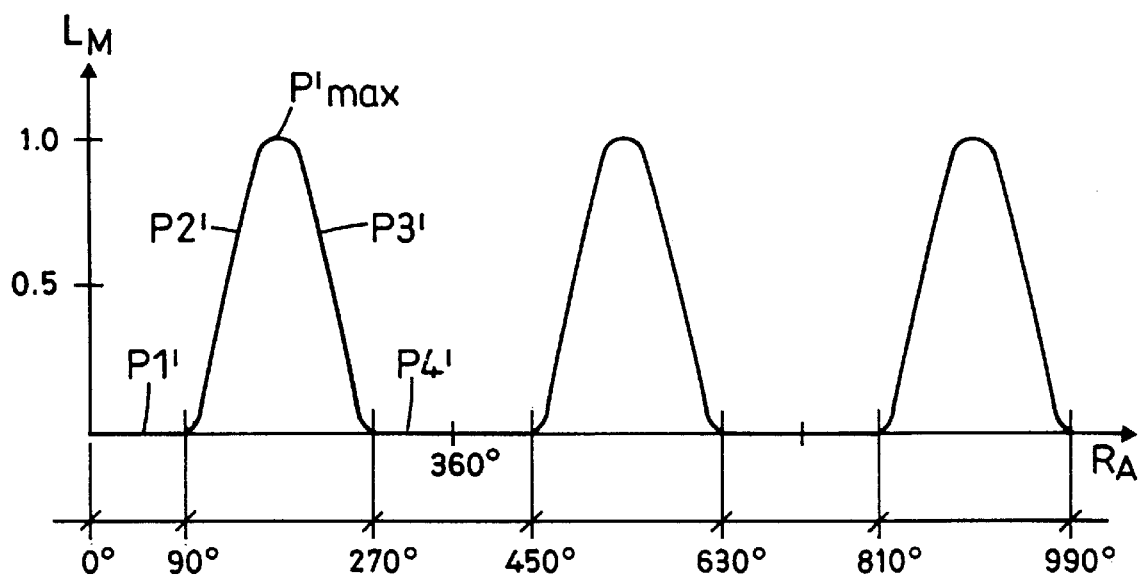
FIG. 12 is a representation of several graphs of the movement pattern of the inner tube through interaction with the control member of FIG. 5.

FIG. 12 shows a graphic representation of a addition of the rotational phases plotted in a coordinate system in connection with the movement patterns and resultant movements. Starting with $P_I$ (point of intercept) the coordinate system at a point of intersection on the abscissa referred to as $R_A$ (rotation angle), a number of rotations are shown here. On the ordinate referred to as $L_M$ (lifting motion), the respective "open" and "closed" positions of the suction opening 21 in the guide tube 20 can be seen as a result of the axially directed movement of the control member 45 by means of the curved track 50. The various rotation phases P1 to P4 of shaft 94 and the resultant movement patterns in axial direction of the control member 45 and the coupling member 35 together with the inner tube will now be described:

As shown schematically in FIG. 12, beginning from the point of intersection $P_I$, in the first rotation phase P1' at a rotation angle $R_A$ from 0° to 90° no movement $L_M$ is registered and thus no axial displacement of any of components 45, 35, and 30 takes place, so that during this phase, the suction opening 21 in the guide tube 20 remains in open position (first reference point).

In the following second rotation phase P2' about rotation angle $R_A$ from 90° to 180°, a first movement $L_M$ is realized which effects an axial displacement of components 45, 35 and 30 until the end position designated with $P'_{max}$. In this phase, the suction opening 21 of the guide tube 20 is sealed by the inner tube 30 which moves axially to the closing position, shown in FIG. 5 (second reference point).

In the following third rotation phase P3', about rotation angle from 180° to 270°, beginning from the end position $P'_{max}$, a reversal of the first motion $L_M$ occurs and results in an axial displacement of the components 45, 35 and 30 such that the inner tube 30 subsequently clears the suction opening 21 and returns to the resting position as shown in FIG. 4.

The suction opening 21 is in open position during the following fourth rotation phase P4', about rotation angle $R_A$ from 270° to 360° and/or when the shaft 94 together with rotation body 65 rotates about rotation angle $R_A$ from 270° to 450°.

The device according to the invention 150 ensures a relatively vibration-free operation even at high cutting rate while yet attaining optimal performance as far as aspiration of tissue particles is concerned. In addition to the high cutting rate, a precise control of the electric motor drive 95 ensures also a small number of single cuts so that its application is possible also at so-called problem areas.

While the invention has been illustrated and described as embodied in a device for use in ophthalmologic procedures, it is not intended to be limited to the details shown since various modifications and structural changes may be made without departing in any way from the spirit of the present invention. What is claimed as new and desired to be protected by letters Patent is set forth in the appended claims:

What is claimed is:

1. A device for use in ophthalmologic surgery for suctioning, cutting and removing portions of the vitreous humor and/or tissue particles, comprising:

a housing defining a longitudinal axis;

a guide tube disposed at the housing for insertion into a hollow space of the vitreous humor, said guide tube having a distal end forming a suction opening;

an inner tube received coaxially in the guide tube;

a drive; and a control member operatively connected with the drive, and receiving the inner tube, for moving the inner tube in the direction of the longitudinal axis between a resting position in which the suction opening of the guide tube is cleared to allow withdrawing the vitreous humor and/or tissue particles and a closing position in which the suction opening is sealed, said control member being configured to allow a movement of the inner tube in the guide tube in the direction of the longitudinal axis from the resting position to the closing position and back to the resting position by translating a rotational movement of the drive into a linear movement of the inner tube, and to refrain from acting on the inner tube at rotational movement of the drive when the inner tube is in the resting position.

2. The device of claim 1, and further comprising a coupling member for linking the inner tube to the control member, and a rotation body having one end operatively connected to a shaft of the drive and another end operatively connected to the control member, whereby the control member is constrained at all times to rotate with the rotation body, said rotation body having a pin for engagement in a curved track formed about an outer periphery of the control member so as to implement a conjoint displacement in axial direction of the control member and the inner tube relative to the suction opening in dependence on the configuration of the curved track.

3. The device of claim 2, wherein at each rotation of the rotation body about the longitudinal axis at rotation angle from 0° to 360°, the inner tube is moved by the control member in axial direction at least once from the resting position to the closing position and back to the resting position.

4. The device of claim 3, wherein at each rotation of the rotation body about the longitudinal axis at rotation angle from 0° to 360°, the inner tube is moved by the control member in axial direction only at a rotation angle of the rotation body in the range approximately 90° to 270°.

5. The device of claim 2, wherein the rotation body includes two spaced-apart fork arms disposed at a side confronting the control member and directed towards the control member, said pin being secured to one of the fork arms for engagement in the curved track.

6. The device of claim 5, wherein the fork arms extend in axial direction over the control member and have confronting inner walls of a circular arc shaped configuration in correspondence to an outer diameter of the control member.

7. The device of claim 2, wherein the control member has a cylindrical core of a diameter which is smaller than an outer diameter of the control member, with the curved track on the control member bounded by the cylindrical core, and two side walls extending circumferentially in parallel relationship, said side walls configured with two semicircular first segments and two curved semicircular second segments formed integrally with the first segments.

8. The device of claim 1, wherein the first segments extend orthogonal to the longitudinal axis and the second segments is so connected to the cylindrical core as to extend approximately curved at an inclination in the direction of a rear wall of the control member, with the first and second segments defining the circumferential side walls for the curved track.

9. The device of claim 2, and further comprising an intermediary piece mounted to the housing, and a headpiece mounted to the intermediary piece and accommodating the guide tube with contained inner tube, said headpiece configured for placement over the intermediary piece and secured by a rotation about the longitudinal axis via a quick release lock.

10. The device of claim 9, wherein the headpiece has a hollow cylindrical recess for engagement of the coupling member, said coupling member having one end operatively connected the control member and another end formed with a flange which is constraint to prevent the coupling piece from rotating.

11. The device of claim 10, wherein the coupling member has a plate for positive engagement of the plate in a groove of the control member, said headpiece forming with the coupling member a structural unit which is so movable in axial direction toward the intermediary piece that a conjoint rotation of the headpiece with the intermediary piece and the coupling piece about the longitudinal axis results in an interaction with the control member via the plate.

12. The device of claim 9, wherein the intermediary piece is configured for receiving the rotation body and the control member, said control member having an axial groove for engagement of a pin which is mounted to the intermediary piece for preventing a rotation of the control member.

13. The device of claim 9, wherein the coupling member is provided with a connection piece for attachment of an aspiration line, said intermediary piece having a slot-shaped axial recess and a bore in communication with the recess for guiding the aspiration line to the outside.

14. The device of claim 9, wherein the headpiece has a locking cam for positive engagement in a bore formed on an outer periphery of the intermediary piece when the headpiece is placed over the intermediary piece and turned about an angle of approximately 90°.

15. The device of claim 2, wherein a revolution of the rotation member is subdivided in rotation phases, whereby a) in a first rotation phase about a rotation angle between approximately 0° to 90°, the control member remains idle so that the inner tube is stationary at a distance to the suction opening;

b) in a second rotation phase about a rotation angle from 90° to 180°, the control member is moved with the inner tube in axial direction in the closing position;

c) in a third rotation phase about a rotation angle from 180° to 270°, the control member returns with the inner tube to the starting position to clear the suction opening;

d) in a fourth rotation phase about a rotation angle from 270° to 360°, the control member remains in the starting position in which the inner tube is positioned at a distance to the suction opening.

16. The device of claim 15, and further comprising a rotation sensor which is operatively connected to the drive to control a movement pattern of the inner tube relative to the suction opening in correspondence with the rotation phases.

17. The device of claim 16, wherein the movement pattern of the inner tube is so controllable by the rotation sensor and the drive that the inner tube is retainable in the resting position in which the suction opening is cleared.

18. The device of claim 2, wherein the control member has an end face distal to the rotation body, and a recess extending inwardly in axial direction from the end face for receiving the coupling element.

19. The device of claim 18, wherein the coupling member has a plate, said control member provided with a groove arranged at a distance to the end face and extending transversely to a longitudinal extension of the recess for positive engagement of the plate.

20. The device of claim 18, wherein the coupling member is provided with a connection piece projecting into the recess of the control member for attachment of an aspiration line.

21. The device of claim 1, wherein the inner tube is in the resting position for a time period which is at least as long as a time period for the inner tube to move from the resting position to the closing position and back to the resting position.

22. The device of claim 1 wherein the drive is an electric motor.

* * * * *